US012350396B2

(12) United States Patent
Park

(10) Patent No.: US 12,350,396 B2
(45) Date of Patent: Jul. 8, 2025

(54) COMPOSITE POSITIVE AND NEGATIVE POISSON'S RATIO TISSUE ADHESIVES

(71) Applicant: Joon Bu Park, Huntington Beach, CA (US)

(72) Inventor: Joon Bu Park, Huntington Beach, CA (US)

(*) Notice: Subject to any disclaimer, the term of this patent is extended or adjusted under 35 U.S.C. 154(b) by 659 days.

(21) Appl. No.: 17/670,067

(22) Filed: Feb. 11, 2022

(65) Prior Publication Data
US 2023/0256133 A1  Aug. 17, 2023

(51) Int. Cl.
A61L 24/00 (2006.01)
B29C 64/10 (2017.01)
B33Y 10/00 (2015.01)
B33Y 70/00 (2020.01)
B33Y 80/00 (2015.01)
B29K 33/20 (2006.01)
B29L 31/00 (2006.01)

(52) U.S. Cl.
CPC ........ A61L 24/0005 (2013.01); A61L 24/0036 (2013.01); A61L 24/0042 (2013.01); B29C 64/10 (2017.08); B33Y 10/00 (2014.12); B33Y 70/00 (2014.12); B33Y 80/00 (2014.12); A61L 2400/12 (2013.01); A61L 2430/34 (2013.01); B29K 2033/20 (2013.01); B29K 2995/006 (2013.01); B29K 2995/0077 (2013.01); B29K 2995/0082 (2013.01); B29L 2031/7546 (2013.01)

(58) Field of Classification Search
None
See application file for complete search history.

(56) References Cited

U.S. PATENT DOCUMENTS

2005/0004599 A1* 1/2005 McNally-Heintzelman ............... A61L 24/0094
606/213
2007/0155010 A1  7/2007 Farnsworth et al.
(Continued)

FOREIGN PATENT DOCUMENTS

EP      2358318      12/2015
WO  WO 1998/019794   5/1998

OTHER PUBLICATIONS

International Search Report and Written Opinion in International Appln. No. PCT/US2023/62197, mailed on Jun. 22, 2023, 14 pages.
(Continued)

Primary Examiner — Peter A Salamon
(74) Attorney, Agent, or Firm — Fish & Richardson P.C.

(57) ABSTRACT

Some tissue adhesives include a solid having bio-absorbable fibers and at least one of nano-spheres, micro-spheres, nano-tubules, or micro-tubules. A first layer of the solid has a positive Poisson's ratio and a second layer of the solid has a negative Poisson's ratio. In some cases, the second layer has been transformed from a positive Poisson's ratio material to a negative Poisson's ratio material. In some cases, an entire face of the first layer is in contact with an entire face of the second layer. In some cases, the second layer includes one or more pores, at least a portion of the one or more pores containing a secretion from one or more barnacles. In some cases, the secretion is configured to adhere the tissue adhesive to one or more layers of tissue to at least partially close a wound.

12 Claims, 9 Drawing Sheets

(56) References Cited

U.S. PATENT DOCUMENTS

| | | | | |
|---|---|---|---|---|
| 2008/0109034 A1* | 5/2008 | Mather | ............... | A61L 31/14 |
| | | | | 606/214 |
| 2010/0121304 A1* | 5/2010 | Zhou | ............... | A61F 13/82 |
| | | | | 604/360 |
| 2011/0250445 A1* | 10/2011 | Alderson | ............... | C09J 7/29 |
| | | | | 428/343 |
| 2014/0276995 A1 | 9/2014 | Lau et al. | | |
| 2016/0346424 A1 | 12/2016 | Lee et al. | | |
| 2017/0165908 A1 | 6/2017 | Pattinson et al. | | |

OTHER PUBLICATIONS

Bourton, "Barnacles' sticky secret revealed," Oct. 16, 2009, retrieved on May 11, 2022, retrieved from URL <http://news.bbc.co.uk/earth/hi/earth_news/newsid_8309000/8309466.stm>, 2 pages.

Chari, "Life Is Rough (01)—Barnacle cement and blood clotting," Mar. 7, 2017, retrieved on May 11, 2022, retrieved from URL <https://indscicomm.blog/2017/03/07/life-is-rough-01-barnacle-cement-and-blood-clotting/#:~:text=Barnacle%20cells%2C%20that%20are%20responsible%20for%20the%20final,are%20seen%20in%20cement%20hardening%20and%20blood%20clotting>, 18 pages.

DeVries et al., "Paramagnetic Resonance Effect In Viscoelastic Materials," UTEC DO 67-049, Semi-Annual Progress Report, NASA Grant NGR, Jan. 1, 1969, 16 pages.

DeVries et al., "Shrinkage influenced by chain rupture during tensile deformation," Journal of Macromolecular Science, Part B—Physics, 1978, 15(3):409-420.

Liang et al., "Biochemistry of Barnacle Adhesion: An Updated Review," Frontiers in Marine Science, Sep. 10, 2019, 6(565):1-20.

medicaldesignbriefs.com [online], "Specialty Absorbable Polymer Materials Enable Innovative Medical Device Platforms," May 1, 2014, retrieved on May 11, 2022, retrieved from URL <https://www.medicaldesignbriefs.com/component/content/article/mdb/features/applications/19657>, 8 pages.

oceanservice.noaa.gov [online], "What are barnacles?, " Feb. 26, 2021, retrieved on May 11, 2022, retrieved from URL <https://oceanservice.noaa.gov/facts/barnacles.html>, 1 page.

Park et al., "Chain rupture during tensile deformation of nylon 6 fibers," Journal of Macromolecular Science, Part B—Physics, 1978, 15(2):205-227.

Park et al., "Structure changes caused by strain annealing of nylon 6 fibers," Journal of Macromolecular Science, Part B—Physics, 1978, 15(2):229-256.

phys.org [online], "Researchers investigate barnacle adhesive," Aug. 8, 2016, retrieved on May 11, 2022, retrieved from URL <https://phys.org/news/2016-08-barnacle-adhesive.html#:~:text=Barnacles%20exude%20an%20adhesive%20with%20exceptional%20bonding%20properties.,insights.%20It%20was%20a%20typical%20case%20of%20serendipity>, 4 pages.

phys.org [online], "Scientists make powerful underwater glue inspired by barnacles and mussels," Jun. 3, 2021, retrieved on May 11, 2022, retrieved from URL <https://phys.org/news/2021-06-scientists-powerful-underwater-barnacles-mussels.html>, 3 pages.

Trafton, "Bio-inspired, blood-repelling tissue glue could seal wounds quickly," Aug. 9, 2021, retrieved on May 11, 2022, retrieved from URL <https://news.mit.edu/2021/barnacle-glue-wound-seal-0809>, 7 pages.

youtube.com[online], "Inguinal Hernia Repair Surgery, Risks and Outcomes—CHI Health," Feb. 16, 2021, retrieved on May 11, 2022, retrieved from URL <https://www.bing.com/videos/search?q=cut+intestine+during+hernia+repair&&view=detail&mid=63498EB73C71CE89F06463498EB73C71CE89F064&&FORM=VRDGAR&ru=%2Fvideos%2Fsearch%3Fq%3Dcut%2Bintestine%2Bduring%2Bhernia%2Brepair%26qpvt%3Dcut%2Bintestine%2Bduring%2Bhernia%2Brepair%26FORM%3DVDRE>, 70 pages [Video Submission].

Zahiri et al., "Evidence-Based Optimal Fixation During Laparoscopic Hernia Repair: Sutures, Tacks, and Glues," Hernia Surgery, Jun. 12, 2016, pp. 287-295.

Zhang et al., "Chapter 10: 3D printing scaffolds for alveolar bone augmentation," (Ed.)Miron et al., Next-Generation Biomaterials for bone & Periodontal Regeneration, Quintessence Pub., Berlin, Jan. 2019, pp. 141-168.

* cited by examiner

COMPOSITE POSITIVE AND NEGATIVE POISSON'S RATIO TISSUE ADHESIVES

BACKGROUND

The present disclosure relates generally to tissue adhesives that include positive and negative Poisson's ratio materials.

Tissue adhesives are used for various medical procedures such as during surgery to close wounds.

SUMMARY

We describe here tissue adhesives that are formed of a composite of both Negative Poisson's Ratio (NPR) materials and Positive Poisson's Ratio (PPR) materials. A material having a Poisson's ratio greater than zero, e.g., between 0 and 1 or between 0 and 0.5, is defined as a PPR material and a material having a Poisson's ratio less than zero, e.g., between −1 and 0, is defined as an NPR material.

In an aspect, a tissue adhesive includes a solid that includes bio-absorbable fibers and at least one of nano-spheres, micro-spheres, nano-tubules, or micro-tubules. The tissue adhesive includes a first layer of the solid having a positive Poisson's ratio and a second layer of the solid having a negative Poisson's ratio. The second layer has been transformed from a positive Poisson's ratio material to a negative Poisson's ratio material. The entire face of the first layer is in contact with an entire face of the second layer. The second layer includes one or more pores with at least a portion of the one or more pores containing a secretion from one or more barnacles. The secretion being configured to adhere the tissue adhesive to one or more layers of muscle to at least partially close a wound.

In an aspect, a tissue adhesive includes a first layer having a positive Poisson's ratio and a second layer in contact with the first layer. The second layer has a negative Poisson's ratio and the second layer includes a sponge structure having one or more pores with each of the one of more pores containing an adhesive. The second layer is configured to contact one or more layers of muscle to at least partially close a wound.

Embodiments of tissue adhesives can include one or any combination of two or more of the following features.

In some embodiments, at least one of the first layer or second layer include at least one of nano-spheres, micro-spheres, nano-tubules, or micro-tubules.

In some embodiments, the second layer includes bioabsorbable fibers.

In some embodiments, the adhesive includes a secretion from one or more barnacles.

In some embodiments, the second layer has been formed by a conversion from a positive Poisson's ratio material into a negative Poisson's ratio material. In some cases, the first layer include the positive Poisson's ratio material.

In some embodiments, the first layer is adjacent to the second layer.

In some embodiments, the first layer includes a metal or a polymer.

In some embodiments, the second layer includes a polymer.

In some embodiments, the second layer is configured to be disposed over the one or more layers of tissue to at least partially close the wound.

In some embodiments, the first layer includes a non-bioabsorbable material and the second layer includes a bioabsorbable material.

In an aspect, a method of forming a tissue adhesive includes forming a solid having a positive Poisson's ratio, the solid comprising bioabsorbable fibers. The method includes converting a portion of the solid into a structure having a negative Poisson's ratio by introducing one or more pores into the portion of the solid. After the conversion, the solid includes a first layer having a positive Poisson's ratio and a second layer having a negative Poisson's ratio. The first layer and the second layer are in contact with each other. The method includes disposing an adhesive into the one or more pores of the solid to form the tissue adhesive.

In some embodiments, the solid includes at least one of nano-spheres, micro-spheres, nano-tubules, or micro-tubules.

In some embodiments, forming the solid includes printing the solid using an additive manufacturing technique. In some cases, printing the solid using the additive manufacturing technique includes printing the solid with a 3D printer.

In some embodiments, the method includes cutting the tissue adhesive to one or more predetermined sizes.

In some embodiments, the method includes stretch-annealing the solid.

In some embodiments, disposing the adhesive into the one or more pores includes disposing a secretion from one or more barnacles into the one or more pores. In some cases, the method includes obtaining the one or more barnacles from a marine environment. In some cases, the method includes providing a flat glass sheet with one or more openings and placing the one or more barnacles proximal to each of the one or more openings. In some cases, the method includes extracting the secretion from the one or more barnacles through each of the openings.

In some embodiments, the method includes applying the tissue adhesive to one or more layers of tissue to at least partially close a wound. In some cases, applying the tissue adhesive to one or more layers of tissue includes applying the second layer over at least a portion of the one or more layers of tissue. In some cases, applying the tissue adhesive to one or more layers of tissue includes curing the tissue adhesive. In some cases, applying the tissue adhesive to one or more layers of tissue comprises applying the tissue adhesive during a hernia surgery. In some cases, applying the tissue adhesive during the hernia surgery includes applying the tissue adhesive using a laparoscope during the hernia surgery. In some examples, applying the tissue adhesive to one or more layers of tissue includes applying the tissue adhesive to one or more layers of a hard tissue.

The tissues adhesives described herein can provide one or more of the following advantages.

By including pores of a sponge structure that contain adhesive, the tissue adhesives described herein allow adhesive to seep out of the pores which forms a stronger connection with the surrounding tissue compared to tissue adhesives without pores or sponge structures.

By using a layer of bioabsorbable materials in contact with the tissue of the patient in combination with a layer of bioabsorbable material or non-bioabsorbable material, the tissue adhesives described herein are able to at least partially absorb into the tissue of the patient while the non-bioabsorbable material maintains the structural integrity of the tissue adhesive. In examples where both layers include absorbable materials, the entire tissue adhesives described herein can be at least partially absorbed into the surrounding tissue which eliminates the need for surgeons to remove the tissue adhesive after the initial placement.

By including bioabsorbable fibers (e.g., collagen) in the tissue adhesive, the tissue adhesives described herein can be stronger than tissue adhesives without bioabsorbable fibers.

By using a composite of PPR and NPR materials, the tissue adhesives described herein can be lighter and equal to or stronger than tissue adhesives formed using only PPR materials.

By including nano and/or micro-sized spheres and/or tubules, the tissue adhesives described herein can be lighter than tissue adhesives without nano and/or micro-sized spheres and/or tubules.

By using a composite of PPR and NPR materials, the tissue adhesives described herein do not contract or expand when curing as much as tissues adhesives formed using only PPR materials. This in turn, transfers less strain from the tissue adhesive to the surrounding tissue and provides a more comfortable patient experience compared to tissues adhesives formed using only PPR materials.

By using a sponge structure, the tissue adhesives described herein can be softer and more compliant compared to hard tissue adhesives.

By printing a layer of the tissue adhesive using a 3D printing technique, the architecture and microstructure of the layer can be specifically designed such that the tissues adhesives described herein can efficiently contain adhesive and form a bonded connection with the surrounding tissue.

By architecting the tissue adhesive to have an overall Zero Poisson's ratio behavior (e.g., where the overall Poisson's ratio is between −0.1 and 0.1), the tissue adhesives described herein can transfer less strain to the patient's tissue.

By including a material with a shape memory property, the tissue adhesives described herein can expand and contract using temperature differences. This can be advantageous because it enables the tissues adhesives to self-contract (e.g., without external contact) to help reduce the size of the wound. In examples where this feature is combined with an overall Zero Poisson's ratio behavior, the tissue adhesives described herein can contract in a direction perpendicular to the wound while having very little or negligible expansion or contraction in a direction parallel to the wound. This can help provide a more comfortable patient experience compared to tissues adhesives without this property.

By using barnacle adhesives in the tissue adhesive, the bonded connection between the tissue adhesive and the surrounding tissue can be stronger than tissue adhesives that do not include barnacle adhesives. Another advantage of using barnacle adhesives is that barnacle adhesives are generally compatible with a saline environment similar to that of the patient's body.

While the above features are described with reference to specific aspects of this disclosure, any of the above features can be used with any of the above aspects.

Other embodiments are within the scope of the claims.

DETAILED DESCRIPTION

We describe here tissue adhesives that are formed of a composite of both Negative Poisson's Ratio (NPR) materials and Positive Poisson's Ratio (PPR) materials. A material having a Poisson's ratio greater than zero, e.g., between 0 and 1 or between 0 and 0.5, is defined as a PPR material and a material having a Poisson's ratio less than 0, e.g., between −1 and 0, is defined as an NPR material.

Figure 1:
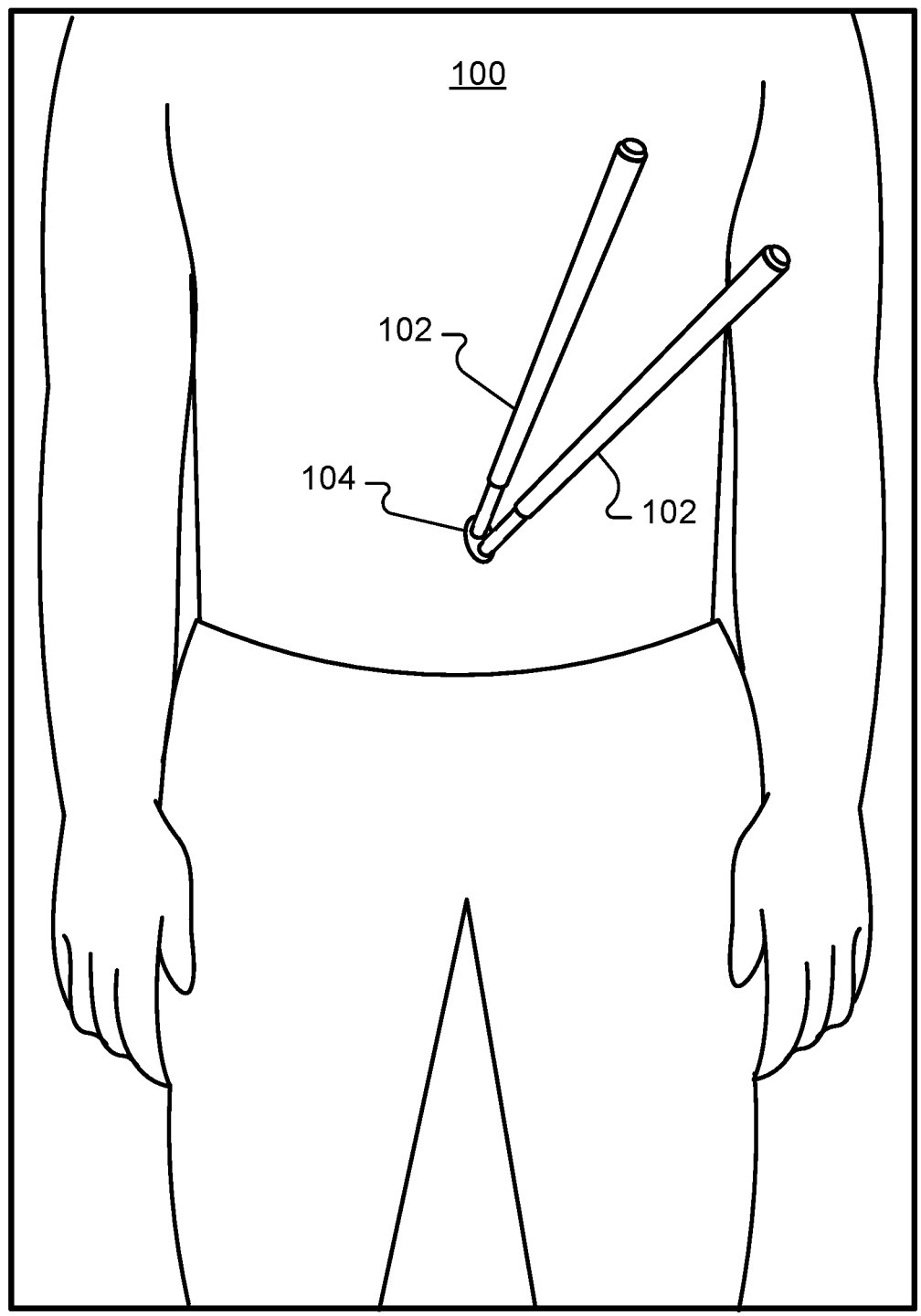
FIG. 1 is an illustration of a patient undergoing a hernia surgery.

FIG. 1 is an illustration of a patient 100 undergoing a laparoscopic surgery to repair an abdominal hernia. Laparoscopic surgery is a minimally invasive surgery where a surgeon (not shown) inserts one or more laparoscopes 102 through one or more small incisions 104, e.g., in the patient's abdominal area of the body. In the context of incisions 104, "a small incision" generally means that the size of the incision is as small as possible while allowing the diameter of the laparoscopes 102 to pass through the incision 104. The use of small incisions compared to larger incisions, e.g., incisions sized such that a surgeon can fit other tools and/or their hands through the larger incision, is advantageous because it allow for faster recovery times compared to larger incisions.

Figure 2:
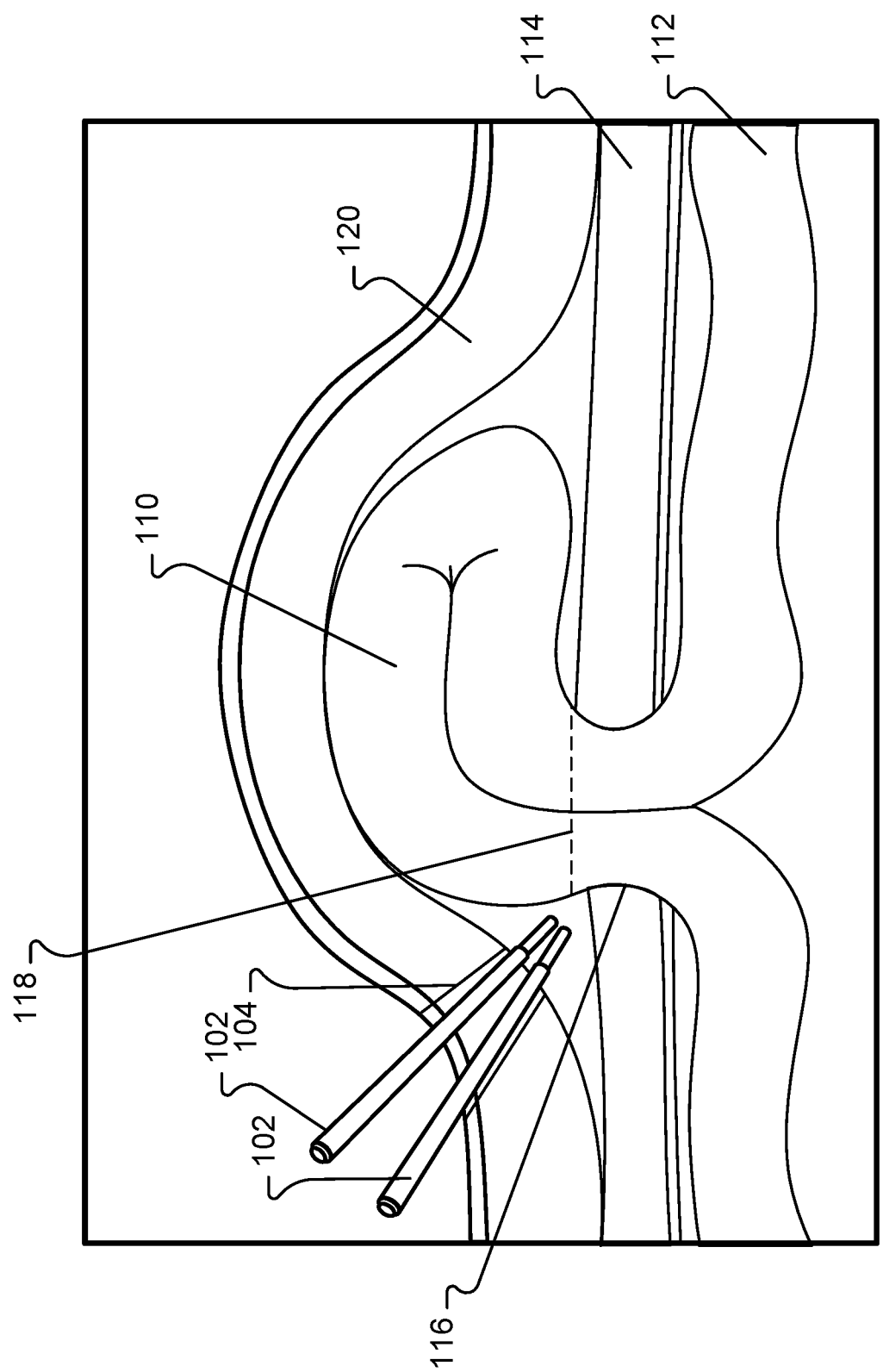
FIG. 2 is an illustration of a hernia.

FIG. 2 is an illustration of a hernia 110. In this example, the hernia 110 represents a portion of the patient's intestine 112 that has penetrated through a layer of the patient's abdominal wall (represented by a first layer of tissue 114) and is trapped between the abdominal wall 114 and a second layer of tissue 120. A portion of the intestine 112 penetrates through an wound 116 in the abdominal wall to define the hernia 110. In some examples, the hernia 110 is formed due to excess stress and/or strain on the abdominal wall. The abdominal wall 114 includes one or more layers of tissue or muscle (e.g., peritoneum).

Surgeons generally have at least two ways to repair the hernia 110. In one approach, the surgeon can push the portion of the intestine 112 defining the hernia 110 back through the wound 116 so that the entire intestine 112 is on a single side of the abdominal wall (e.g., the side internal to the patient 100 which defines the abdominal cavity). In another approach, the surgeon can cut the portion of the intestine 112 defining the hernia 110 at a cut line 118 and stitch or suture the intestine 112 back together. Generally, the first approach is preferred because it is less invasive but the second approach is sometimes appropriate, e.g., if the length of the portion of the intestine 112 defining the hernia is too long (e.g., longer than can reasonably fit within the patient's abdominal cavity).

In some examples, the laparoscope 102 includes a lumen for inserting cameras and/or surgical tools into the hernia region. For example, the surgeon can insert a camera into a lumen of the laparoscope 102 to view the hernia 110 and/or view the wound 116. In some examples, the laparoscope 102 includes a surgical tool inserted through the lumen to enable surgical manipulation of the intestine 112 defining the hernia 110. For example, the surgeon can contact the intestine 112 defining the hernia 110 using the surgical tool and direct it back through the wound 116. In some examples, the surgeon manipulates the laparoscope 102 (e.g., by hand or by a robotically controlled arm) to contact the intestine 112 (e.g., the portion of the intestine 112 defining the hernia) by engaging one or more griping arms of the surgical tool with the intestine 112. In some examples, the surgeon manipulates the laparoscope 102 to cut the intestine 112 (e.g., the portion of the intestine defining the hernia) by engaging one or more cutters of the surgical tool with the intestine 112 at the cut line 118 and stitching or suturing the intestine 112 back together.

Figure 3:
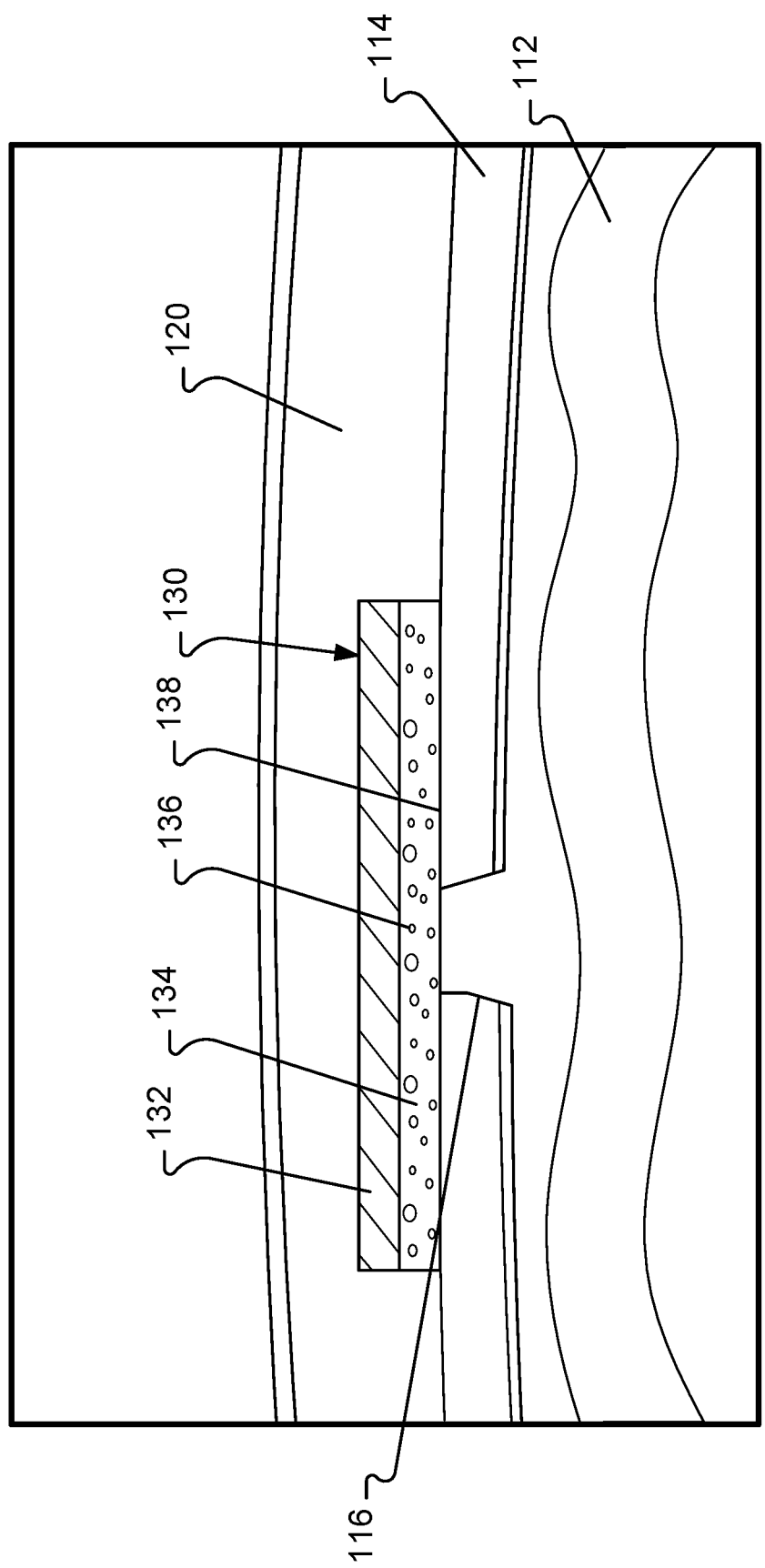
FIG. 3 is an illustration of a tissue adhesive being used to close a wound.

FIG. 3 is an illustration of a repaired hernia, e.g., following a surgical intervention in which a surgeon has either pushed the portion of the intestine 112 defining the hernia 110 back through the wound 116 and/or has cut and sutured/stitched the intestine 112. Following the repair, a tissue adhesive 130 is placed over the wound 116 to close the wound 116 and seal the patient's abdominal cavity. In some examples, the surgeon inserts the tissue adhesive 130 through the lumen of the laparoscope 102 and positions the tissue adhesive 130 over the wound 116 using a surgical tool (e.g., one or more gripping arms). In some examples, the surgeon passes the tissue adhesive 130 through the incision 104 and then uses a surgical tool to position the tissue adhesive 130 over the wound 116.

Figure 4:
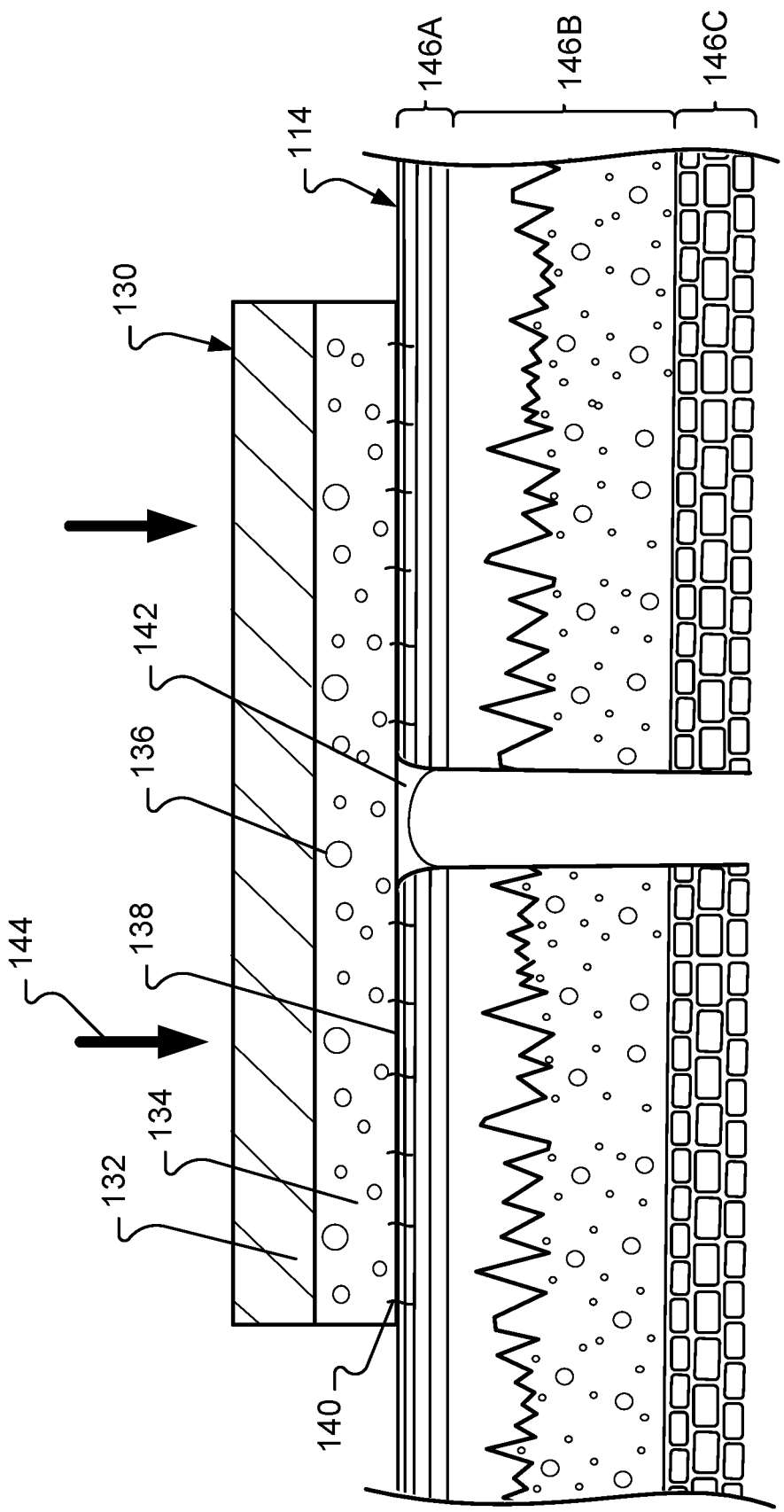
FIG. 4 is a close-up illustration of a tissue adhesive.

Referring to FIGS. 3 and 4, the tissue adhesive 130 can include a solid (e.g., a solid adhesive) with a first layer 132 and a second layer 134, with one or both of the layers composed of a material that is adhesive to the tissue 114. The first layer 132 is disposed adjacent to the second layer 134 such that an entire face of the first layer 132 is in contact with an entire face of the second layer 134. The tissue adhesive 130 is positioned in contact with the tissue 114 and spanning the wound 116. In this example, the tissue 114 includes one or more layers of tissue 146A, 146B, and 146C.

In some examples, the first layer 132 of the tissue adhesive 130 includes a material and/or geometric structure that enables the first layer 132 to exhibit PPR behavior (also known as "non-auxetic behavior"), meaning that the first layer 132 contracts along a first direction when stretched along a second perpendicular direction. The kinematics of PPR materials are described with reference to FIG. 7. For example, the first layer 132 can include material (e.g., a metal or a polymer) that exhibits PPR behavior. In some examples, the first layer 132 includes a material defining a lattice structure that enables the first layer 132 to exhibit PPR behavior. For example, the first layer 132 can include a material having a non-reentrant honeycomb lattice structure that exhibits PPR behavior. For example, In some examples, the second layer 134 of the tissue adhesive 130 includes a material and/or geometric structure that enables the second layer 134 to exhibit NPR behavior (also known as "auxetic behavior"), meaning that the second layer 134 expands along a first direction when stretched along a second perpendicular direction. The kinematics of NPR materials are also described with reference to FIG. 7. For example, the second layer 134 can include a material (e.g., a metal or a polymer) that exhibits NPR behavior. In some examples, the second layer 134 includes a material defining a lattice structure that enables the second layer 134 to exhibit NPR behavior. For example, the second layer 134 can include a material having a reentrant honeycomb lattice structure that exhibits NPR behavior. For example, Depending on the particular materials and/or geometric lattices used in the first and second layers 132, 134 of the tissue adhesive 130, the tissue adhesive 130 can exhibit an overall PPR behavior, a NPR behavior, or a zero Poisson's ratio behavior ("ZPR behavior"). In some examples, ZPR behavior exists when the overall Poisson's ratio of the tissue adhesive 130 is between −0.1 and 0.1.

In some examples, a tissue adhesive 130 exhibiting a ZPR behavior can result from using materials having equal but opposite materials properties and/or geometric lattices of the first and second layers 132, 134. By tailoring the particular material properties and geometric lattices of the first and second layers 132, 134 of the tissue adhesive 130 to achieve an overall ZPR behavior, the expansion and contraction of the tissue adhesive is reduced compared to tissue adhesives formed using only PPR or only NPR materials.

For example, some tissue adhesives, such as tissue adhesives formed of only PPR materials or only NPR materials, can contract and/or expand when adhesive is curing. This contraction and expansion can exert an undesirable strain on the tissue 114. The tissue adhesive 130 can exhibit an overall ZPR behavior which transfers less strain from the tissue adhesive 130 to the tissue 114. This can provide a more comfortable patient experience, and promotes healing of the tissue, compared to tissues adhesives formed using only PPR materials or only NPR materials. In some cases, applying a stress to the tissue adhesive 130 (e.g., by a surgeon) and/or a residual stress within the tissue adhesive 130 (e.g., from curing adhesive) can cause the tissue adhesive to exhibit ZPR behavior.

In some examples, the first layer 132 includes a non-bioabsorbable material and the second layer 134 includes a bioabsorbable material. For example, the first layer 132 can include a non-bioabsorbable material to preserve the structural integrity of the tissue adhesive 130 and the second layer 134 can include a bioabsorbable material to enable the second layer 132 to biodegrade, e.g., to be absorbed by the tissue 114. In some examples, both the first layer 132 and the second layer 134 are bioabsorbable. For example, in such cases, the entire tissue adhesive 130 biodegrades over time as the wound 116 heals, e.g., the tissue 130 absorbs the entire tissue adhesive 130.

As used herein, "non-bioabsorbable" means that the material is not absorbed by the tissue under typical environment conditions and "bioabsorbable" means the material can be absorbed by the tissue under typical environment conditions. As used herein, "typical environmental conditions" means that the tissue adhesive is applied in a generally dry and temperature controlled environment (e.g., a hospital setting or a patient's home).

Various materials can be used with the tissue adhesive 130. For example, the first layer 132 of a tissue adhesive can be a non-bioabsorbable material such as a non-bioabsorbable metal, e.g., titanium or stainless steel, or a non-bioabsorbable polymer, e.g., silicone, nitrile, neoprene, viton, etc. The first layer 132, the second layer 134, or both can be a bioabsorbable material such as a bioabsorbable polymer, e.g., polyglycolide, poly(1-lactide), etc.

In some examples, the first layer 132 can include a PPR material (e.g., the bioabsorbable or non-bioabsorbable metals and/or polymers described above) and the second layer 134 can include a NPR material (e.g., a biocompatible titanium alloy (e.g., Ti6A14V) or other metal or a polymer). In some examples, the second layer 134 is formed only of an NPR material such that the NPR material is in direct contact with the tissue 114. In some examples, the second layer is a composite of an NPR material and a PPR material. For example, the second layer 134 can include a first portion of an NPR material and a second portion of a PPR material, such as a bioabsorbable polymer. The PPR can provide a matrix within which the NPR material is dispersed, e.g., in a particulate structure, in a layered composite structure, or in another type of composite structure. Conversely, the NPR material can provide a matrix within which the PPR material is dispersed.

In some examples, the second layer 134 includes an NPR foam material composed of, e.g., polymer, ceramic, metal NPR material, or combinations thereof. In some examples, the NPR foam material is made of a biocompatible titanium alloy (e.g., Ti6A14V). In some examples, the second layer 134 is formed of a material that has been transformed from a material exhibiting PPR behavior (a "non-auxetic material") to a material exhibiting NPR behavior (an "auxetic material") (e.g., by a combination of heat and pressure as described with reference to FIG. 7 below). In a specific example, the second layer 134 is formed of a titanium alloy that has been transformed from a non-auxetic titanium alloy to an auxetic titanium alloy, e.g., by application of heat, compressive pressure, or both to the non-auxetic titanium alloy.

In some examples, the second layer 134 defines one or more pores 136 that define recesses (or void space) within the second layer 134. For example, the NPR foam material of the second layer 134 can include pores 136 that define a sponge structure. In examples where a bioabsorbable portion is in direct contact with the tissue 114, the bioabsorbable portion can include the pores 136 that define the sponge structure (e.g., the pores 136 can be defined by a bioabsorbable polymer such as a polyglycolide or poly(1-lactide)-based polymer.

As shown in FIGS. 3 and 4, the pores 136 can be of various (e.g., non-uniform) shapes and sizes. In some examples, the pores 136 can range from nano-sized pores (e.g., between 1 nanometer (nm) and 1 micrometer (μm)) to micro-sized pores (e.g., between 1 μm and 1 millimeter (mm)). In some examples, the pores 136 can be sphere-shaped, ellipsoid-shaped, or tubule-shaped. For example, the pores 136 can be nano-sized and/or micro-sized spheres, ellipsoids, or tubules.

In some examples, at least one of the first layer 132 and second layer 134 includes at least one of nano-spheres, micro-spheres, nano-tubules, or micro-tubules. For example, both the first layer 132 and the second layer 134 can include nano-spheres, micro-spheres, nano-tubules, or micro-tubules as described above.

In some examples, the first layer 132 includes a PPR material and the second layer 134 includes a material that has been transformed from the PPR material of the first layer 132. That is, the first layer 132 and the second layer 134 include the same material composition but the second layer 134 has been transformed from a PPR material to a NPR material and the first layer 132 remains the PPR material.

In some examples, at least one of the first layer 132 and second layer 134 includes bio-absorbable fibers. For example, the second layer 134 can include collagen. In some examples, the collagen can be strengthened by a stretch-annealing process. Examples of stretch-annealing processes are described in one or more of the following references which are hereby incorporated by reference in their entirety: J. B. Park, K. L. DeVries and W. O. Statton, "Chain rupture during tensile deformation of nylon 6 fibers," J. Macromol. Sci.-Physics, B15, 205-227, 1978; J. B. Park, K. L. DeVries and W. O. Statton, "Structure changes caused by strain annealing of nylon 6 fibers," J. Macromol. Sci.-Physics, B15, 229-256, 1978; and K. L. DeVries, W. O. Statton and J. B. Park, "Shrinkage influenced caused by strain annealing of nylon 6 fibers," J. Macromol. Sci.-Physics, B15, 409-420, 1978.

In some examples, at least some of the pores 136 contain an adhesive. For example, the pores 136 can contain a bioabsorbable adhesive (e.g., fibrin sealant, bovine serum albumin & glutaldehyde, etc) and/or a non-bioabsorbable adhesive (e.g., cyanoacrylate, etc.). For example, the adhesive can be non-bioabsorbable adhesive such as a cyanoacrylate-based adhesive (e.g., an adhesive that contains cyanoacrylate). In some examples, the adhesive contains at least one of a cyanoacrylate, a fibrin sealant, and/or bovine serum albumin & glutaldehyde deposited within at least some of the pores 136. In some examples, the adhesive is a bio-absorbable adhesive that includes a 2-part protein sealant and thrombin.

In some examples, a surgeon deposits adhesive into the pores 136 and positions the tissue adhesive 130 on the tissue 114 of the patient 100 over the wound 116. In this way, the second layer 134 is configured to be disposed over the one or more layers of tissue or muscle to cover the wound 116. In some examples, each of the one or more pores 136 contain an adhesive.

In some examples, the pores 136 can contain an adhesive such as 2-octyl-cyanoacrylate (e.g., from a commercial product such as Dermabond® or Surgiseal®) and/or n-2-butyl-cyanoacrylate (e.g., from a commercial product such as Histoacryl Blue® or Periacryl®). In some examples, the pores can contain an adhesive such as zinc phosphate, zinc polycarboxylate, glass ionomer, resin sealant (unfilled and/or filled), resin cement, or composite resin filling material.

Table 1 shows examples of adhesives that can be used with the tissue adhesive 130 and their respective mechanical properties. In Table 2, the compressive strength and tensile strength are represented in megapascals (MPa), the tensile modulus is represented in gigapascals (GPa), and the facture toughness ($K_{IC}$) is represented in megapascals multiplied by square root meter ($MPa*m^{1/2}$).

TABLE 1

Example adhesive materials and their respective mechanical properties.

| Materials | Compressive strength (MPa) | Tensile strength (MPa) | Tensile modulus (GPa) | Toughness $K_{IC}$ ($MPa * m^{1/2}$) |
|---|---|---|---|---|
| Zinc phosphate | 80-100 | 5-7 | 13 | ~0.2 |
| Zinc polycarboxylate | 55-85 | 8-12 | 5-6 | 0.4-0.5 |
| Glass ionomer | 70-200 | 6-7 | 7-8 | 0.3-0.4 |
| Resin sealant unfilled | 90-100 | 20-25 | 2 | 0.3-0.4 |
| Resin sealant filled | 150 | 30 | 5 | — |
| Resin cement | 100-200 | 30-40 | 4-6 | — |
| Composite resin filling material | 350-400 | 45-70 | 15-20 | 1.6 |

In some examples, when applying the tissue adhesive 130 to the tissue 114, a surgeon applies pressure to the tissue adhesive (e.g., by pressing down on the tissue adhesive 130 in the direction shown by arrows 144 to compress the second layer 134 of the tissue adhesive between the first layer 132 and the tissue 114). The adhesive seeps out of the pores 136 due to the pressure and contacts the tissue 114. Once cured (e.g., once a sufficient amount of time has passed (e.g., 1 minutes) or once the adhesive is exposed to heat, ultraviolet (UV) light, or another suitable stimulus), the tissue adhesive becomes bonded to the tissue 114, thereby connecting the tissue to the left-hand-side of the wound 116 to the tissue to the right-hand-side of the wound 116. In this way, the tissue adhesive 130 closes the wound 116, and the intestine 112 no longer can pass through the wound 116 once the tissue adhesive 130 is adhered to the tissue 114. In some examples, the tissue adhesive 130 spans all or at least a portion of the wound 116.

In some examples, at least some of the pores 136 of the second layer 134 of the tissue adhesive extend from a bottom surface 138 of the second layer 134 and extend various depths into the second layer 134. For example, by extending from the bottom surface 138, adhesive contained within the pores 136 can seep out onto the tissue and form a strong bonded connection 140 (shown in FIG. 4) between the second layer 134 and the tissue 114. In the example shown in FIG. 4, the adhesive is at least partially bio-absorbable (e.g., includes fibrin sealant) so that the adhesive is at least partially absorbed into the tissue 114 which aids in the bonded connection of the tissue adhesive 130 to the tissue 114.

In some examples, at least some of the pores 136 contain a tissue growth agent (e.g., bacitracin) that seeps out of the pores 136 and forms a web 142 within the wound 116 when the tissue adhesive 130 is adhered to the tissue 114. The web 142 can help facilitate a growth of tissue within the wound 116 between the tissue on each side of the wound 116. In some examples, the tissue growth agent is mixed with adhesive. In some examples, only adhesive is used (e.g., no tissue growth agent is used).

In some examples, at least one of the first layer 132 and the second layer 134 includes a material having a shape memory property. For example, the material of the first and/or second layer 132, 134 can include nickel titanium alloys (e.g., Nitinol) that deforms when subject to a temperature difference and reverts to a pre-deformed state when the temperature difference is no longer applied. In some examples, at least a portion of the first and second layers 132, 134 can include Nitinol such that the tissue adhesive 130 can expand when heated to above a body temperature of the patient (e.g., above 98.6 degrees Fahrenheit) and contract when the heat is removed. Such a feature enables the surgeon to position the tissue adhesive 130 on the tissue 114 in a heated state (e.g., while heated to a temperature above 98.6 degrees Fahrenheit), then, due to the temperature of the tissue 114 being approximately 98.6 degrees Fahrenheit, the tissue adhesive 130 will begin to contract. This contraction can help to reduce the size of the wound 116 while the adhesive is curing so that once the adhesive is cured, the wound 116 is smaller than when the surgeon first applied the tissue adhesive 130. In some examples, tissues adhesives that include a metal alloy (e.g., Nitinol) can enable the tissue adhesive to be used to close hard tissue closures such as closures involving bone (e.g., rib-cages).

In some examples, the sponge structure of the tissue adhesive 130 can be both architected such that an overall ZPR behavior is achieved and designed to exhibit a shape memory property. For example, a tissue adhesive 130 having a sponge structure formed of Nitinol that is architected to have ZPR behavior can be heated and cooled to achieve expansion and contraction along a first direction while a second perpendicular direction does not expand or contact. Such a feature enables the surgeon to position the tissue adhesive 130 on the tissue 114 in a heated state (e.g., while heated to a temperature above 98.6 degrees Fahrenheit), then, due to the temperature of the tissue 114 being approximately 98.6 degrees Fahrenheit, the tissue adhesive 130 will begin to contract in one direction while not contracting in the second perpendicular direction. This contraction can help to reduce the size of the wound 116 while reducing strain in the perpendicular direction that may not be helpful in closing the wound 116.

In some examples, the adhesive contained in the pores includes a secretion from one or more barnacles. A barnacle is a type of arthropod constituting the subclass Cirripedia and is related to crabs and lobsters. Barnacles typically produce a cement secretion that helps them attach to both hard and soft substrates underwater (e.g., boat hulls, pier pilings, mammals, etc.). A unique property of this cement secretion is that the secretion forms a strong bond underwater which is typically a challenging environment for adhesives. In the context of the tissue adhesive 130, the pores 136 can contain cement secretion from barnacles which enables the tissue adhesive 130 to form a strong bonded connection to the tissue 114. In this way, the secretion is configured to adhere the tissue adhesive 130 to one or more layers of tissue 114 to at least partially close the wound 116.

In some examples, using barnacle adhesives is advantageous because the barnacle adhesive is compatible with a saline environment similar to that of the patient's body. In some examples, synthetic adhesives that have similar properties and/or composition to natural (or organic) barnacle adhesive can be used in addition to, or instead of, natural barnacle adhesives.

Figure 5:
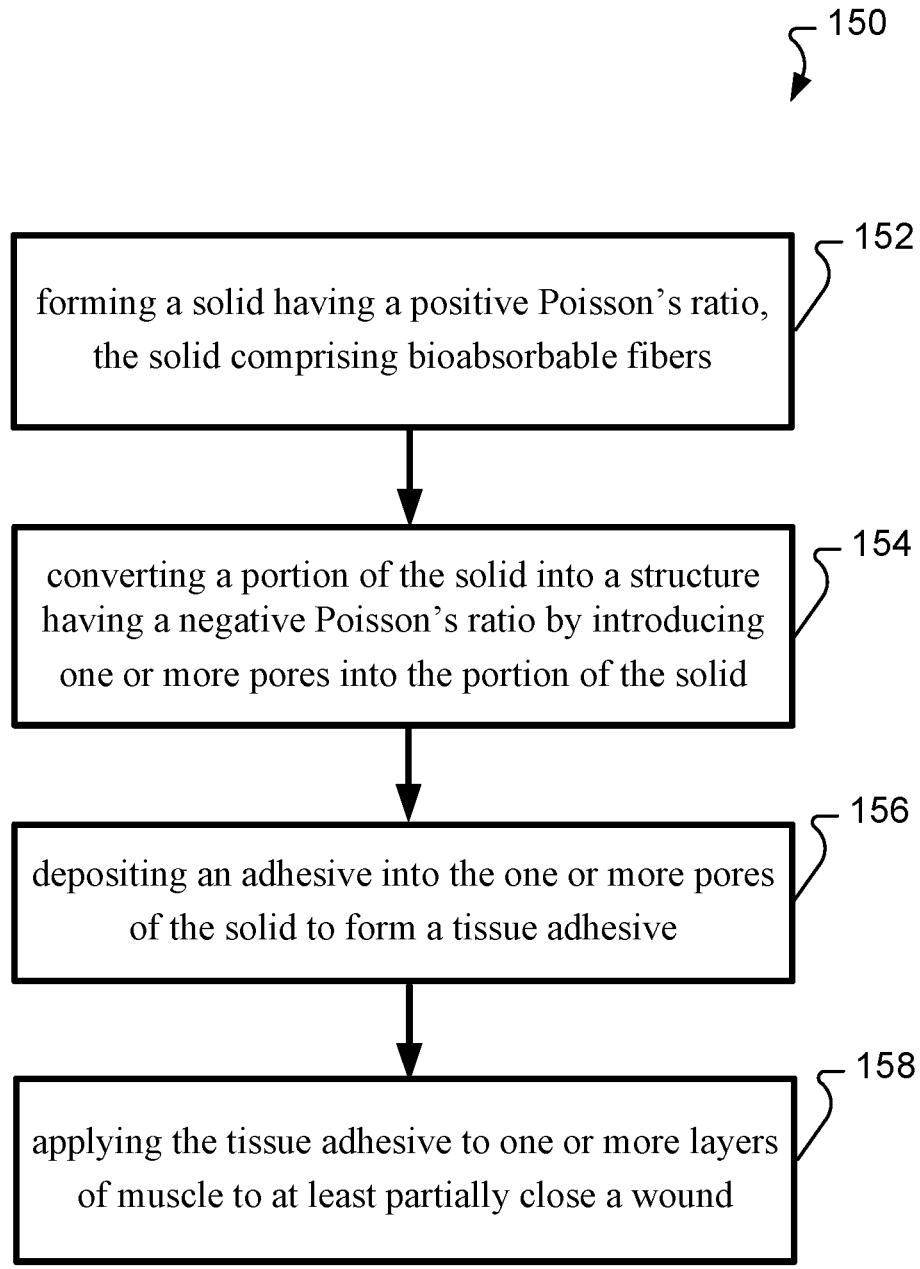
FIG. 5 is a flowchart.

FIG. 5 is a flowchart of a method 150 for forming a tissue adhesive and applying the tissue adhesive to at least partially close a wound. One or more steps of the method 150 can be performed by a surgeon or a layperson. In some examples, a surgeon performs the steps of method 150 to form the tissue adhesive 130 described with reference to FIGS. 3 and 4 and repair the abdominal hernia 110 described with reference to FIGS. 1 and 2.

At 152, the method 150 includes forming a solid having a PPR and bioabsorbable fibers. For example, the solid is formed using an additive manufacturing technique, e.g., printed using a 3D printer. For example, the first layer 132 and/or the second layer 134 of the tissue adhesive 130 can be formed by additive manufacturing, e.g., printed using a 3D printer. Examples of 3D printers and 3D printing processes are described with reference to FIG. 8.

At 154, the method includes converting a portion of the solid into a structure having a NPR by introducing one or more pores into the portion of the solid. For example, an additive manufacturing tool, e.g., a 3D printer, can print or otherwise form a particular sponge structure of the pores 136 of the second layer 134. The sponge structure can cause the material to be have an NPR. For example, printing a sponge structure that is associated with NPR can give the second layer 134 an NPR characteristic. In some examples, printing a reentrant honeycomb sponge structure into the second layer 134 allows the second layer 134 to exhibit PPR behavior, NPR behavior, and/or ZPR behavior when subject to a mechanical deformation or temperature difference.

In some examples, the sponge structure of the second layer 134 is specifically designed such a large volume of adhesive can be contained within the pores 136. For example, the sponge structure can be architected using a pattern of reentrant honeycombs with a large volume of open space (e.g., defining the pores 136). In some examples, the pore volume can be between 70%-90% of the volume of second layer 134.

In some examples, after the conversion described in 154, the solid includes a first layer 132 having a PPR behavior and a second layer 134, in contact with the first layer 132, and having a NPR behavior. In some cases, the first layer 132 and the second layer 134 are in contact with each other as shown in FIGS. 3 and 4.

At 156, the method includes disposing an adhesive into the one or more pores of the solid. For example, a person can deposit an adhesive (e.g., cyanoacrylate, fibrin sealant, etc.) into the pores 136. In some examples, a person soaks the second layer 134 in a container of adhesive to absorb the adhesive into the pores 136. In some examples, a person uses a syringe with a needle to inject the adhesive into at least some of the pores 136.

At 158, the method includes applying the tissue adhesive to one or more layers of tissue to at least partially close a wound. For example, a surgeon applies the tissue adhesive 130 to the tissue 114 (e.g., the abdominal wall) described with reference to FIGS. 3 and 4 to cover the wound 116. In some examples, the surgeon at least partially covers the tissue 114 with the second layer 134 of the tissue adhesive 130. For example, at least a portion of the tissue 114 is in direct mechanical contact with the second layer 134 of the tissue adhesive 130 as shown in FIGS. 3 and 4.

In some examples, applying the tissue adhesive to one or more layers of tissue includes curing the tissue adhesive. For example, the adhesive within the pores 136 can seep out of the second layer 134 and contact the tissue 114. In turn, the adhesive cures (e.g., hardens) when either a particular time has elapsed (e.g., 1 minute) or a particular event has occurred (e.g., heat, UV light used to cure a UV curable adhesive, or another suitable stimulus). In some examples, the surgeon illuminates the adhesive with UV light using a UV light positioned on an end of a laparoscope 102.

In some examples, applying the tissue adhesive to one or more layers of tissue includes applying the tissue adhesive during a hernia surgery. For example, a surgeon applies the tissue adhesive 130 during an abdominal hernia surgery as described with reference to FIGS. 1 and 2. In some cases, applying the tissue adhesive during the hernia surgery includes applying the tissue adhesive using a laparoscope during the hernia surgery. For example, a surgeon applies the tissue adhesive 130 using one or more gripping arms of the laparoscopes 102. In some examples, applying the tissue adhesive to one or more layers of tissue includes applying the tissue adhesive to one or more layers of a hard tissue (e.g., bone).

In some examples, the method 150 includes cutting the tissue adhesive to one or more predetermined sizes. For example, a person cuts (e.g., using scissors or a blade) tissue adhesives of a particular size out of a larger sheet. In some examples, the tissue adhesive is cut to be 1 inch by 1 inch square, 2 inch by 2 inch square, 1 inch by 2 inch rectangles, etc. In this way, the tissue adhesive can be cut to various sizes as appropriate for particular surgical procedures and wound sizes. In some examples, smaller and/or larger sizes are required for particular sized wounds (e.g., for smaller and/or larger wounds, respectively). In some examples, different shapes are required for particular shaped wounds (e.g., rectangular tissue adhesives, circular tissue adhesives, triangular tissue adhesives, etc.). In some examples, different aspect ratios are required for particular sized wounds (e.g., tissue adhesives having a length to width ratio of 2, tissue adhesives having a length to width ratio of 5, etc.) Generally, the tissue adhesive can be cut to any shape, size, and aspect ratio for any particular application.

In some examples, the method 150 includes stretch-annealing the solid. As described above with reference to FIGS. 3 and 4, examples of stretch-annealing processes are described in one or more of the following references which are hereby incorporated by reference in their entirety: J. B. Park, K. L. DeVries and W. O. Statton, "Chain rupture during tensile deformation of nylon 6 fibers," J. Macromol. Sci.-Physics, B15, 205-227, 1978; J. B. Park, K. L. DeVries and W. O. Statton, "Structure changes caused by strain annealing of nylon 6 fibers," J. Macromol. Sci.-Physics, B15, 229-256, 1978; and K. L. DeVries, W. O. Statton and J. B. Park, "Shrinkage influenced caused by strain annealing of nylon 6 fibers," J. Macromol. Sci.-Physics, B15, 409-420, 1978.

In some examples, disposing the adhesive into the pores 136 includes disposing a secretion from one or more barnacles into the pores 136. For example, a user can deposit a secretion from one or more barnacles into at least a portion of the pores 136 using a syringe with a needle. In some examples, a user can dispose a secretion from one or more barnacles into at least a portion of the pores 136 by immersing the tissue adhesive 130 into the secretion from one or more barnacles.

In examples where barnacles are used, the method 150 can include obtaining the one or more barnacles from a marine environment. For example, a user can obtain barnacles from an underwater environment by scraping the barnacles from a hard surface (e.g., a boat hull or a pier piling, etc.) or from a soft surface (e.g., a mammal, etc.). In some cases, the method 150 includes providing a flat sheet, e.g., a glass sheet, with one or more openings (e.g., holes (e.g., holes extending though the sheet), recesses (e.g., recesses defining a reservoir), etc.) and placing the one or more barnacles proximal to each of the one or more openings. For example, a user can place a barnacle within each such that the barnacle can excrete a secretion which contacts the inner radial surface of the openings. In turn, a user can extract the secretion from the one or more barnacles by extracting (e.g., by a blade) the secretion from the inner radial surface of each of the openings. Then a user can inject the secretion into the pores 136 using one of the methods described above.

In some cases, the openings are recesses that define reservoirs. In such cases, the method can include placing the one or more barnacles proximal to each of the one or more recesses. For example, a user can place a barnacle near an opening of each recess such that the barnacle can excrete a secretion which is collected in each reservoir. In turn, a user can extract the secretion from the one or more barnacles by extracting (e.g., siphoning by a syringe) the secretion from the reservoirs of the flat sheet. Then a user can inject the secretion into the pores 136 using one of the methods described above.

Figure 6:
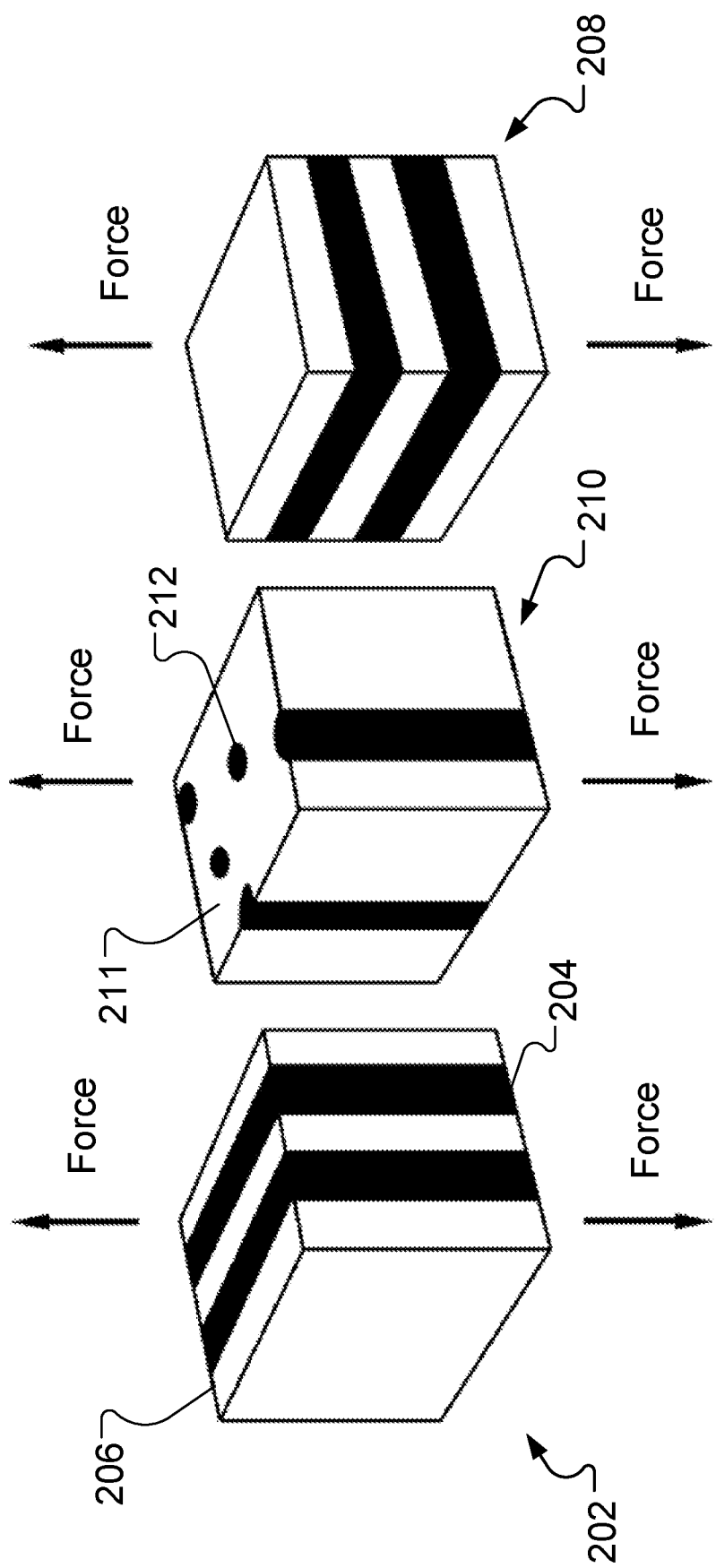
FIG. 6 is an illustration of composite materials.

FIG. 6 illustrates examples of NPR-PPR composite materials. An NPR-PPR composite material 202 is a laminar composite including alternating layers 204 of NPR material and layers 206 of PPR material. The layers 204, 206 are arranged in parallel to a force to be exerted on the composite material 202. Although the layers 204, 206 are shown as having equal width, in some examples, a laminar composite can have layers of different widths.

An NPR-PPR composite material 208 is a laminar composite including alternating layers of NPR material and PPR material, with the layers arranged perpendicular to a force to be exerted on the material 208. In some examples, the layers of a laminar composite are arranged at an angle to the expected force that is neither perpendicular nor parallel.

An NPR-PPR composite material 210 is a matrix composite including a matrix phase 211 of NPR material with a reinforcement phase 212 of PPR material. In the material 212, the reinforcement phase 212 includes fibers of the PPR material; in some examples, the reinforcement phase 212 can include particles or other configuration. In some examples, NPR-PPR composite materials can have a matrix phase of a PPR material with a reinforcement phase of an NPR material.

Figure 7:
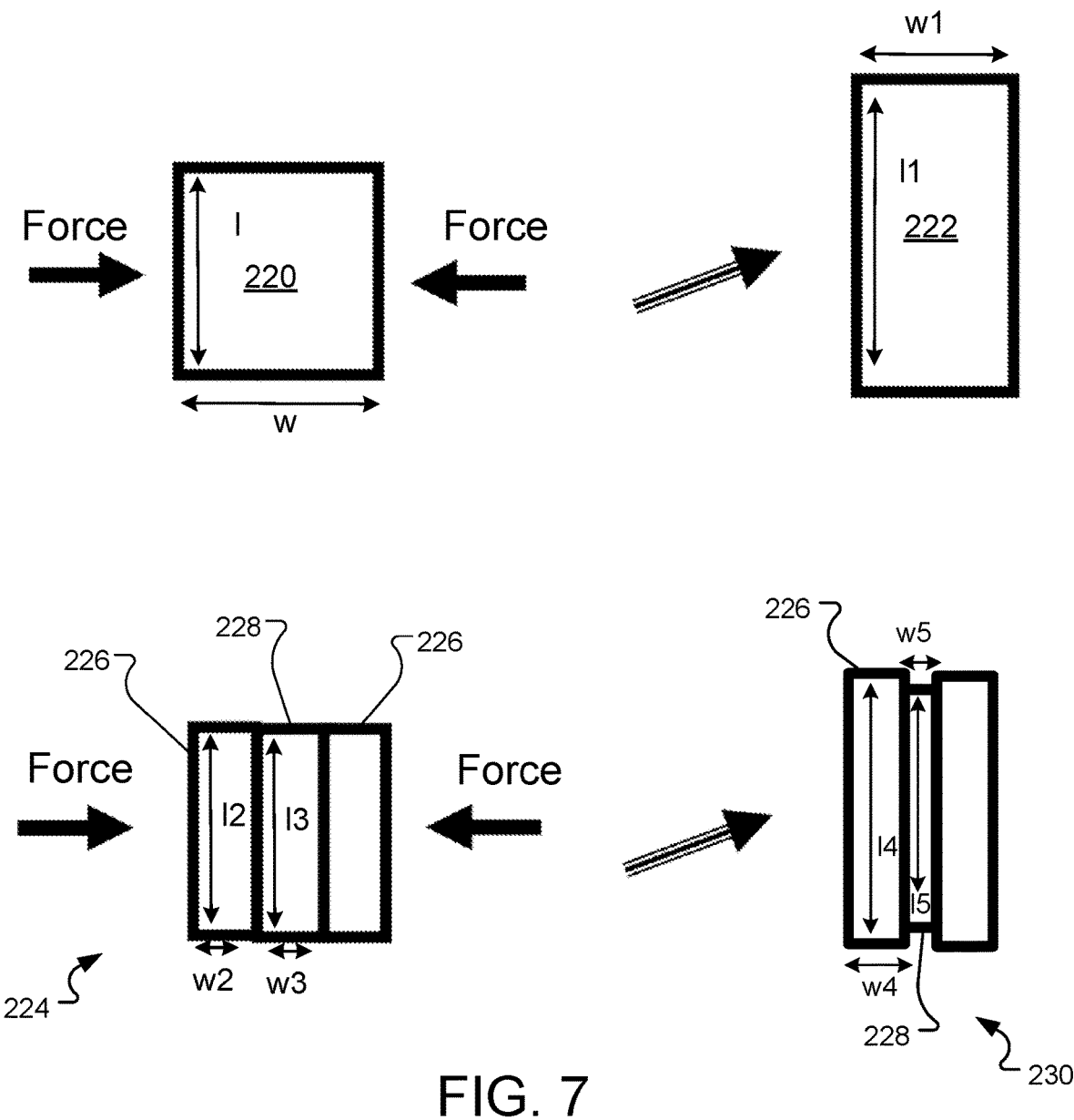
FIG. 7 is an illustration of a material with a PPR and a composite material.

FIG. 7 illustrates the mechanical behavior of PPR and NPR-PPR composite materials. A hypothetical block 220 of PPR material, when compressed along its width w, deforms into a shape 222. The width w1 of the compressed block 222 is less than the width w of the uncompressed block 220, and the length l1 of the compressed block 222 is greater than the length l of the uncompressed block: the material compresses along the axis to which the compressive force is applied and expands along a perpendicular axis.

A block 224 of NPR-PPR composite material includes a region 228 of NPR material sandwiched between two regions 226 of PPR material. When the block 224 of composite material is compressed along its width, the material deforms into a shape 230. The PPR regions 226 compress along the axis of compression and expand along a perpendicular axis, e.g., as described above for the block 220 of PPR material, such that, e.g., the width w2 of a region 226 of uncompressed PPR material compresses to a smaller width w4 and the length l2 of the region 226 expands to a greater length l4. In contrast, the NPR region 228 compresses along both the axis of compression and along the perpendicular axis, such that, e.g., both the width w3 and length l3 of the uncompressed NPR region 228 are greater than the width w5 and length l5 of the compressed NPR region 228.

Figure 8:
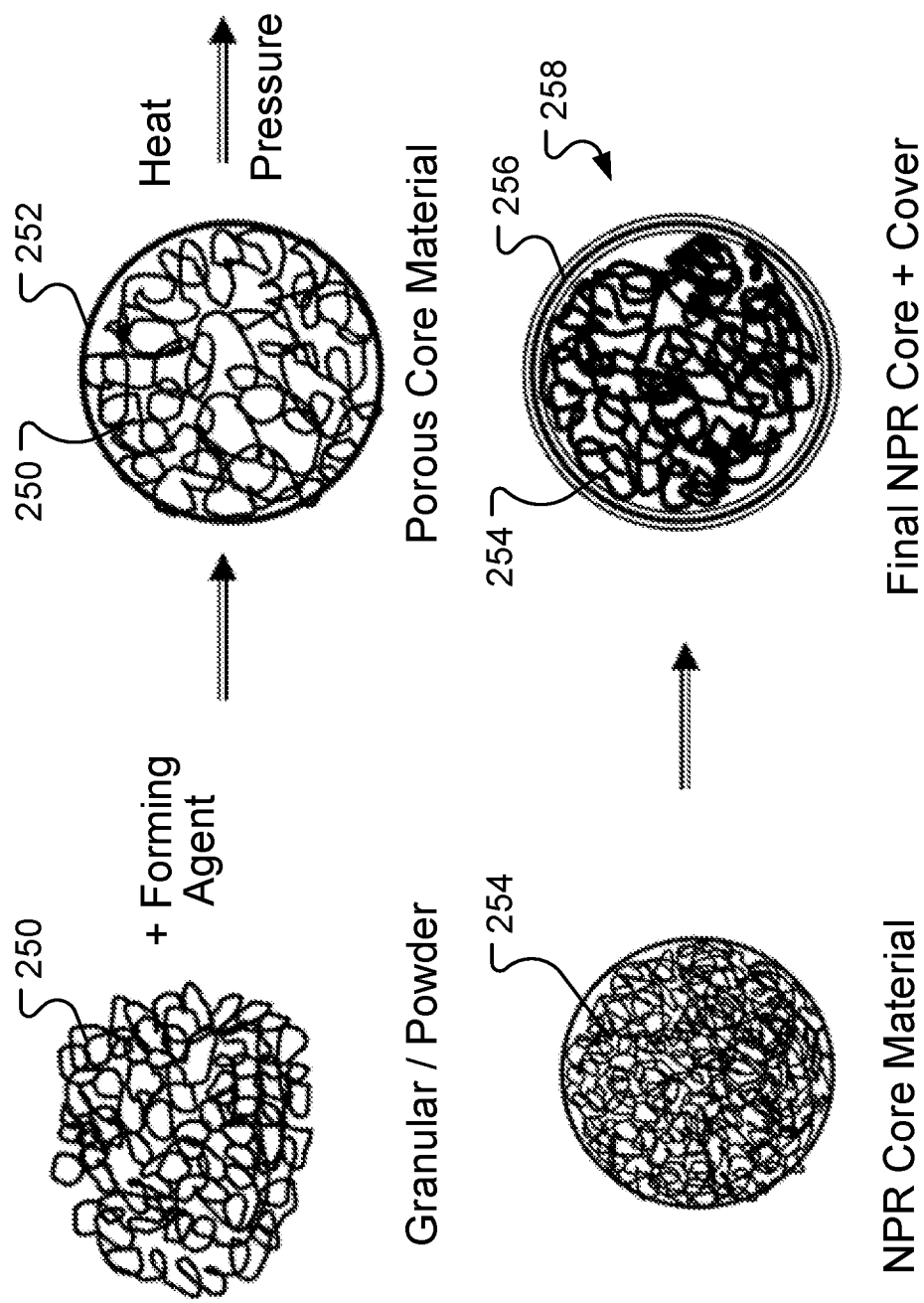
FIG. 8 is a diagram of a process for forming an NPR-PPR composite material.

FIG. 8 is a diagram of a process for forming an NPR-PPR composite material. A granular or powdered material, such as a polymer material (e.g., a rubber) is mixed with a foaming agent to form a porous material 250. The porous material 250 is placed into a mold 252. Pressure is applied to compress the material 250 and the compressed material is heated to a temperature above its softening point. The material is then allowed to cool, resulting in an NPR foam 254. In some examples an NPR foam 254 is used with a PPR material.

For example, the medical devices described herein can be composites of PPR and NPR materials. For example, the tissue adhesive 130 described with reference to FIGS. 3 and 4 can include an NPR foam second layer 134 combined with a PPR material first layer 132. In this example, the NPR foam 254 is combined with the PPR material (e.g., generally represented using numeral 256 in FIG. 8) and heat and pressure is applied again to cure the final material into the NPR-PPR composite 258. In this way, the layered composite of the tissue adhesive 130 is formed by applying heat and pressure to the tissue adhesive 130.

Other methods can also be used to fabricate a tissue adhesive formed of an NPR-PPR composite material. For example, various additive manufacturing (e.g., 3D printing) techniques, such as stereolithography, selective laser sintering, or other appropriate additive manufacturing technique, can be implemented to form a tissue adhesive device formed of an NPR-PPR composite.

Figure 9:
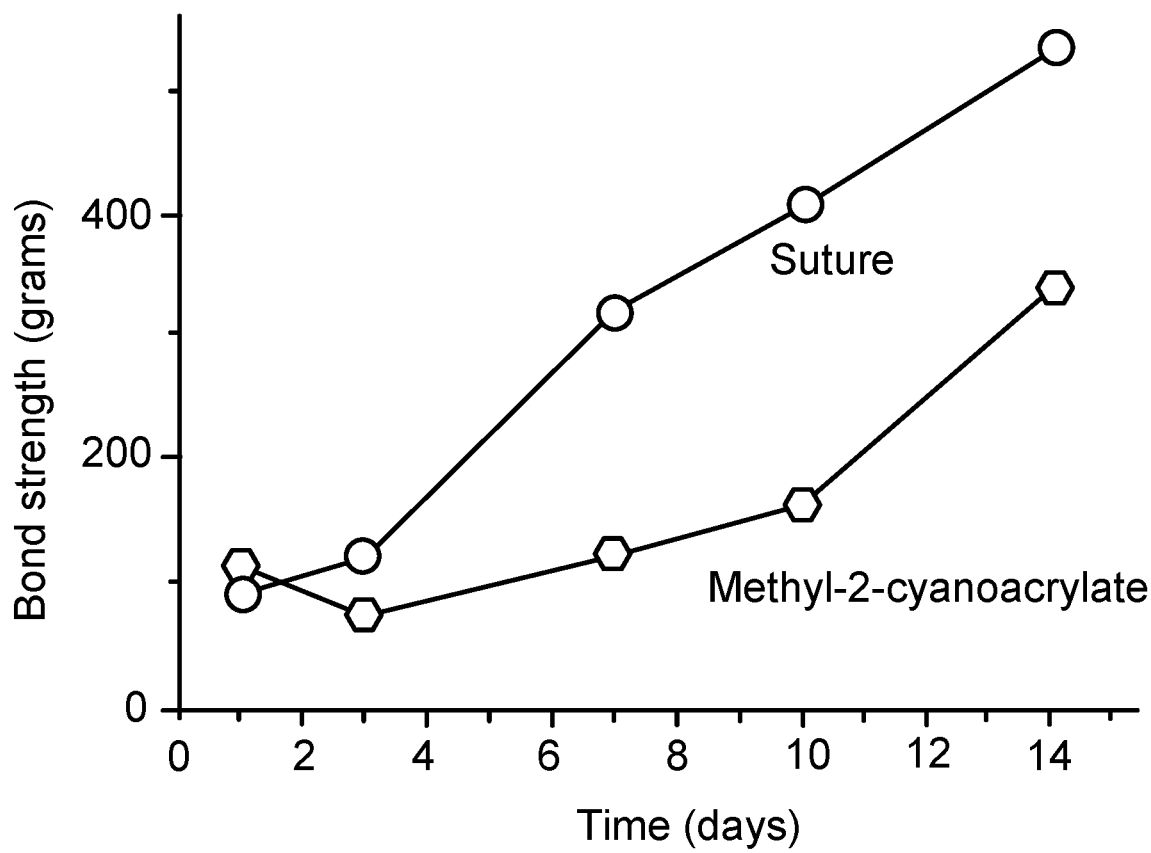
FIG. 9 is a plot of the bond strength of a tissue adhesive using methyl-2-cyanoacrylate compared to the bond strength of a suture versus time.

FIG. 9 is a plot of the bond strength of a tissue adhesive using methyl-2-cyanoacrylate compared to the wound strength of a suture versus time. FIG. 9 illustrates that a 350 gram (approximately) wound closure strength is achieved after 14 days have elapsed since a tissue adhesive that includes a methyl-2-cyanoacrylate adhesive was applied to the tissue. In the example shown, the bond strength generally increases over time as the tissue adhesives are absorbed into the tissue and/or as the tissue grows into and/or around the tissue adhesives. When the tissue adhesive is applied to the tissue, the strength of a suture compared to a tissue adhesive is comparable.

While the examples described herein relate to abdominal hernia surgery, the tissue adhesives described herein can be used with other types of hernia surgeries. For example, the tissue adhesives described herein can be used with upper stomach and groin surgeries. Generally, the tissue adhesives described herein can be used to treat hernia surgeries located anywhere on the patient's body.

While the examples described herein relate to laparoscopic surgery, the tissue adhesives described herein can be used for other types of surgeries. For example, the tissue adhesives described herein can be used to treat topical incisions on an external layer of skin of a patient. The tissue adhesives described herein can be used to treat wounds as a part of open surgery (e.g., open heart surgery). Generally, the tissue adhesives described herein can be used to treat wounds located anywhere on the patient's body.

While the examples described herein relate to closing soft tissue wounds (e.g., the abdominal wall, the tissue adhesives described herein can be used with hard tissues (e.g., bone). Generally, the tissue adhesives can include first and second layers of stiff materials (e.g., metal alloys) that enable large closure forces to be applied to hard tissues. In other examples, the tissue adhesives can include first and second layers of compliant/flexible materials (e.g., polymers) that allow the tissues adhesives to conform to the applied tissue.

While the examples described herein relate to treating a human patient, the tissue adhesives described herein can be used with other types of patients. For example, the tissue adhesives described herein can be used on animals and mammals. Generally, the tissue adhesives described herein can be used to treat any animal or mammal having a layer of tissue to be closed.

As illustrated by the example embodiments described herein, tissue adhesives can include NPR-PPR composite materials and can be used to treat abdominal hernia surgeries. In some examples, tissues adhesives include a layer of a NPR foam material that contains adhesive that enables improved adhesion to tissue compares to tissue adhesives that do not include pores and do not include adhesive deposited within the pores.

What is claimed is:

1. A tissue adhesive comprising:
   a first layer having a positive Poisson's ratio; and
   a second layer in contact with the first layer, the second layer having a negative Poisson's ratio, the second layer comprising a sponge structure having one or more pores, wherein each of the one of more pores contain an adhesive;
   wherein the second layer is configured to contact one or more layers of tissue to at least partially close a wound, and
   wherein at least one of the first layer or second layer comprise at least one of nano-spheres, micro-spheres, nano-tubules, or micro-tubules.

2. The tissue adhesive of claim 1, wherein the second layer comprises bioabsorbable fibers.

3. The tissue adhesive of claim 1, wherein the adhesive comprises a secretion from one or more barnacles.

4. The tissue adhesive of claim 1, wherein the second layer has been formed by a conversion from a positive Poisson's ratio material into a negative Poisson's ratio material.

5. The tissue adhesive of claim 1, wherein the first layer is adjacent to the second layer.

6. The tissue adhesive of claim 1, wherein the first layer comprises a metal or a polymer.

7. The tissue adhesive of claim 1, wherein the second layer comprises a polymer.

8. The tissue adhesive of claim 1, wherein the second layer is configured to be disposed over the one or more layers of tissue to at least partially close the wound.

9. The tissue adhesive of claim 1, wherein the first layer comprises a non-bioabsorbable material and the second layer comprises a bioabsorbable material.

10. The tissue adhesive of claim 1, wherein the solid is formed by an additive manufacturing technique.

11. The tissue adhesive of claim 1, wherein an entire face of the first layer is in contact with an entire face of the second layer.

12. The tissue adhesive of claim 3, wherein the secretion is configured to adhere the tissue adhesive to the tissue.

\* \* \* \* \*